US011160881B2

(12) United States Patent
Rangaramanujam et al.

(10) Patent No.: US 11,160,881 B2
(45) Date of Patent: Nov. 2, 2021

(54) DENDRIMER COMPOSITIONS FOR USE IN ANGIOGRAPHY

(71) Applicant: The Johns Hopkins University, Baltimore, MD (US)

(72) Inventors: Kannan Rangaramanujam, Baltimore, MD (US); Siva Pramodh Kambhampati, Baltimore, MD (US); Gerard Lutty, Baltimore, MD (US); Rishi Sharma, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 51 days.

(21) Appl. No.: 16/608,691

(22) PCT Filed: Apr. 27, 2018

(86) PCT No.: PCT/US2018/029882
§ 371 (c)(1),
(2) Date: Oct. 25, 2019

(87) PCT Pub. No.: WO2018/201007
PCT Pub. Date: Nov. 1, 2018

(65) Prior Publication Data
US 2020/0179537 A1  Jun. 11, 2020

Related U.S. Application Data

(60) Provisional application No. 62/490,936, filed on Apr. 27, 2017.

(51) Int. Cl.
| A61K 49/00 | (2006.01) |
| A61B 3/10 | (2006.01) |
| A61B 3/12 | (2006.01) |
| A61B 5/00 | (2006.01) |
| A61K 45/06 | (2006.01) |

(52) U.S. Cl.
CPC ...... *A61K 49/0054* (2013.01); *A61K 49/0034* (2013.01); *A61K 49/0043* (2013.01); *A61B 3/102* (2013.01); *A61B 3/1241* (2013.01); *A61B 5/0066* (2013.01); *A61K 45/06* (2013.01)

(58) Field of Classification Search
CPC ........... A61K 49/0054; A61K 49/0034; A61K 49/0043; A61K 45/06; A61K 49/0021; A61B 3/102; A61B 3/1241; A61B 5/0066; A61P 27/02
See application file for complete search history.

(56) References Cited

U.S. PATENT DOCUMENTS

| 6,624,245 | B2 | 9/2003 | Wallace |
| 7,674,781 | B2 | 3/2010 | Sheardown |
| 9,345,781 | B2 | 5/2016 | El-Sayed |
| 2003/0180250 | A1 | 9/2003 | Chauhan |
| 2008/0031848 | A1 | 2/2008 | Konradi |
| 2010/0015231 | A1 | 1/2010 | Lu |
| 2010/0160299 | A1 | 6/2010 | Baker |
| 2011/0018929 | A1 | 1/2011 | Kawashima |
| 2011/0034422 | A1 | 2/2011 | Rangaramanujam |
| 2012/0003155 | A1 | 1/2012 | Rangaramanujam |
| 2012/0177593 | A1 | 7/2012 | Baker, Jr. |
| 2012/0263672 | A1 | 10/2012 | Artzi |
| 2013/0123330 | A1 | 5/2013 | Lu |
| 2013/0136697 | A1 | 5/2013 | Rangaramanujam |
| 2013/0165771 | A1 | 6/2013 | Ni |
| 2015/0352230 | A1 | 12/2015 | Mullen |
| 2017/0043027 | A1 | 2/2017 | Rangaramanujam |
| 2017/0119899 | A1 | 5/2017 | Sujatha |
| 2018/0256480 | A1 | 9/2018 | Deng |

FOREIGN PATENT DOCUMENTS

| CN | 103804693 | 5/2014 |
| CN | 103999853 | 8/2014 |
| RU | 2093165 | 10/1997 |
| RU | 2367525 | 6/2007 |
| RU | 2521338 | 8/2012 |
| WO | 0018394 | 4/2000 |
| WO | 2004/058272 | 7/2004 |
| WO | 2004058272 | 7/2004 |
| WO | 2005/055926 | 11/2004 |
| WO | 2005055926 | 11/2004 |
| WO | 2006/069719 | 7/2006 |
| WO | 2006069719 | 7/2006 |
| WO | 2006/115547 | 11/2006 |
| WO | 2006115547 | 11/2006 |
| WO | 2009/046446 | 4/2009 |
| WO | 2009046446 | 4/2009 |
| WO | 2009/142754 | 1/2010 |
| WO | 2009142754 | 1/2010 |
| WO | 2010/147831 | 12/2010 |
| WO | 2010147831 | 12/2010 |
| WO | 2011/011384 | 7/2011 |
| WO | 2011011384 | 7/2011 |
| WO | 2011/123591 | 10/2011 |
| WO | 2011123591 | 10/2011 |
| WO | 2012/037457 | 3/2012 |

(Continued)

OTHER PUBLICATIONS

Anonymous, "Poly (amidoamine)", *Wikipedia*, 1-11 (Mar. 27, 2018).
Baba, et al., "A rat model for choroidal neovascularization using subretinal lipid hydroperoxide injection", *Am. J. Pathol.*, 176(6):3085-3097 (2010).
Bagul, et al., "Heterolayered hybrid dendrimers with optimized sugar head groups for enhancing carbohydrate-protein interactions", *Polymer Chemistry*, 8(35):5354-5366 (2017).
Berger, et al., "Current and future pharmacological treatment strategies in x-linked adrenoleukodystrophy", *Brain Pathol.*, 20(4):845-56 (2010).
Berk, et al., "The promise of N-acetylcysteine in neuropsychiatry", *Trends in Pharmacological Sciences*, 34(3):167-177 (2013).

(Continued)

*Primary Examiner* — Robert S Cabral
(74) *Attorney, Agent, or Firm* — Pabst Patent Group LLP

(57) ABSTRACT

Compounds, compositions, kits and methods for performing angiography related to ocular diseases, are disclosed.

30 Claims, 2 Drawing Sheets

(56) References Cited

FOREIGN PATENT DOCUMENTS

| WO | 2012037457 | 3/2012 |
| --- | --- | --- |
| WO | 2012142470 | 10/2012 |
| WO | 2014026283 | 2/2014 |
| WO | 2014/109927 | 7/2014 |
| WO | 2014109927 | 7/2014 |
| WO | 2014/197909 | 12/2014 |
| WO | 2014197909 | 12/2014 |
| WO | 2015/027068 | 2/2015 |
| WO | 2015027068 | 2/2015 |
| WO | 2015/038493 | 3/2015 |
| WO | 2015038493 | 3/2015 |
| WO | 2015168347 | 11/2015 |
| WO | 2014/178892 | 12/2015 |
| WO | 2014178892 | 12/2015 |
| WO | 2016025741 | 2/2016 |
| WO | 2016/025745 | 4/2016 |
| WO | 2016025745 | 4/2016 |
| WO | 2017/074993 | 5/2017 |
| WO | 2017074993 | 5/2017 |
| WO | 2017139341 | 8/2017 |
| WO | 2019094952 | 5/2019 |

OTHER PUBLICATIONS

Bi, et al., "Synthesis of PAMAM dendrimer-based fast cross-linking hydrogel for biofabrication", *Journal of Biomaterials Science*, 26(11):669-682 (2015).

Bravo-Osuna, et al., "Interfacial Interaction between Transmembrane Ocular Mucins and Adhesive Polymers and Dendrimers Analyzed by surface Plasmon Resonance", *Pharmaceutical Research*, 29(8):2329-2340 (2012).

Cerqueira, et al., "Microglia response and in vivo therapeutic potential of methylprednisolone-loaded dendrimer nanoparticles in spinal cord injury", *Nanoparticles*, 5:738-49 (2013).

Desmettre, et al., "Fluorescence properties and metabolic features of indocyanine green (ICG) as related to angiography", *Survey of Ophthalmology*, 45(1):15-27 (2000).

Dodd, et al., "Putative neuroprotective agents in neuropsychiatric disorders", *Progress in Neuro-Psychopharmacology & Biological Psychiatry*, 42:135-45 (2003).

Engelen, et al., "Bezafibrate lowers very long-chain fatty acids in X-linked adrenoleukodystrophy fibroblasts by inhibiting fatty acid elongation", *J. Inherit. Metab. Dis.*, 35(6):1137-45 (2012).

Fang, et al., "Host—guest chemistry of dendrimer-drug complexes: 7. Formation of stable inclusions between acetylated dendrimers and drugs bearing multiple charges", *J. Phys. Chem. B*, 116:3075-82 (2012).

Grinstaff, et al., "Dendritic macromers for hydrogel formation: Tailored materials for ophthalmic, orthopedic, and biotech applications", *Journal of Polymer Science Part A: Polymer Chemistry*, 46(2):383-400 (2007).

Han, et al., "Convergent Synthesis of PAMAM Dendrimers Containing Tetra (ethyleneoxide) at Core Using Click Chemistry", *Bulletin of the Korean Chemical Society*, 33(10):3501-3504 (2012).

Hossain, et al., "Comparative study of microtubule inhibitors-Estramustine and natural podophyllotoxin conjugated PAMAM dendrimer on glioma cell proliferation", *European Journal of Medicinal Chemistry*, 68:47-57 (2013).

Iezzi, et al., "Dendrimer-based targeted intravitreal therapy for sustained attenuation of neuroinflammation in retinal degeneration", *Biomaterials*, 33(3):979-88 (2012).

Islam, et al., "Controlling the cytokine storm in severe bacterial diarrhea with an oral toll-like receptor 4 antagonist", *Immunology*, 147:178-89 (2015).

Jaszberenyi, et al., "Physicochemical and MRI characterization of Gd3+- loaded polyamidoamine and hyperbranched dendrimers", *J. Bol. Inorg. Chem.*, 12(3):406-420 (2007).

Jonas, et al., "Intravitreal triamcinolone acetonide for exudative age related macular degeneration", *Br. J. Ophthalmol.*, 87(4):462-8 (2003).

Kambhampati, et al., "Systemic and Intravitreal Delivery of Dendrimers to Activated Microglia/Macrophage in Ischemia/Reperfusion Mouse Retinal Microglia Uptake of Dendrimers", *Investigative ophthalmology & visual science*, 56(8):4413-24 (2015).

Kannan, et al., "Dendrimer-based postnatal therapy for neuroinflammation and cerebral palsy in a rabbit model", *Sci. Transl. Med.*, 4(130):130ra46 (2012).

Keane, et al., "Imaging chorioretinal vascular disease", *Eye*, 24(3):422-427 (2010).

Klaassen, et al., "Molecular basis of the inner blood-retinal barrier and its breakdown in diabetic macular edema and other pathological conditions", *Progress in Retinal and Eye Research*, 31(34):19-48 (2013).

Kurtoglu, et al., "Drug release characteristics of PAMAM dendrimer-drug conjugates with different linkers", *Intl. J. Pharma.*, 384(1-2):189-94 (2010).

Lesniak, et al., "Biodistribution of fluorescently labeled PAMAM dendrimers in neonatal rabbits: effect of neuroinflammation", *Mol. Pharma.*, 10(12):4560-71 (2013).

Leukodystropy, National Organization for Rare Disorders, pp. 1-20, https://rarediseases.org/rare-diseases/leukodystrophy/, retrieved from the internet Sep. 5, 2017.

Lintas, et al., "Genome-wide expression studies in autism spectrum disorder, rett syndrome, and down syndrome", *Neurobiol. Disease*, 45:57-68 (2012).

Madaan, et al., "Dendrimers in drug delivery and targeting: Drug-dendrimer interactions and toxicity issues", *J. Pharm. Bioallied Sci.*, 6(3): 139-150 (2014).

Menjoge, et al., "Dendrimer-based drug and imaging conjugates: design considerations for nanomedical applications", *Drug Discov. Today*, 15(5-6):171-185 (2010).

Mignani, et al., "Expand classical drug administration ways by emerging routes using dendrimer drug delivery systems: a concise overview", *Adv. Drug Delivery Rev.*, 65(10):1316-30 (2013).

Mishra, et al., "Dendrimer brain uptake and targeted therapy for brain injury in a large animal model of hypothermic circulatory arrest", *ACS Nano*, 8(3):2134-47 (2014).

Nance, et al., "Systemic dendrimer-drug treatment of ischemia-induced neonatal white matter injury", *Journal of Controlled Release*, 214:112-120 (2015).

Navath, et al., "Dendrimer-drug conjugates for tailored intracellular drug release based on glutathione levels", *Bioconjugate Chem.*, 19(12):2446-53 (2008).

Neal, et al., "Discovery and validation of a new class of small molecule Toll-like receptor 4 (TLR4) inhibitors", *PLoS One*, 8(6): e65779 (2013).

Oelker, et el., "Ophthalmic adhesives: a materials chemistry perspective", *Journal of Materials Chemistry*, 18(22):2521 (2008).

Owens, et al., "Indocyanine green angiography", *The British Journal of Ophthalmology*, 80(3):263 (1996).

Polam, et al., "Effect of chorioamnionitis on neurodevelopmental outcome in preterm infants", *Arch. Pediatr. Adolesc. Med.*, 159(11):1032-5 (2005).

Qian, et al, "Synergistic inhibition of human glioma cell line by temozolomide and PAMAM-mediated miR-21i", *Journal of Applied Polymer Science*, 127(1):570-576 (2012).

Resident, "Injection Methods", Standard Clinical Technique, 2(6): 128-129 (2009). (Japanese Language Document with English Summary).

Ribeiro-Viana et al., "BODIPY-Labeled DC-SIGN—Targeting Glycodendrons Efficiently Internalize and Route to Lysosomes in Human Dendritic Cells", *Biomacromolecules*, 13(10):3209-3219 (2012).

Sadekar, et al., "Transepithelial transport and toxicity of PAMAM dendrimers for oral drug delivery", *Adv. Drug Del Rev.*, 64:571-88 (2012).

Sarin, et al., "Effective transvascular delivery of nanoparticles across the blood-brain tumor barrier into malignant glioma cells", *J. Trans. Med.*, 80(6):1-15 (2008).

Seelbach, et al., "Multivalent dendrimers presenting spatially controlled clusters of binding epitopes in thermoresponsive hyaluronan hydrogels", *Acta Biomaterialia*, 10(10):4340-4350 (2014).

(56) References Cited

OTHER PUBLICATIONS

Sevick-Muraca, et al., "Fluorescence-enhanced, near infrared diagnostic imaging with contrast agents", *Current opinion in Chemical Biology*, 6(5):642-50 (2002).

Sharma, et al., A fast track strategy toward highly functionalized dendrimers with different structural layers: an "onion peel approach", *Polym. Chem.*, 6:1436-1444 (2015).

Sharma, et al., "Low generation polyamine dendrimers bearing flexible tetraethylene glycol as nanocarriers for plasmids and siRNA", *Nanoscale*, 8(9):5106-5119 (2016).

Shiao, et al., "Synthesis of Dense and Chiral Dendritic Polyols Using Glyconanosynthon Scaffolds", *Molecules Online*, 21(4):448 (2016).

Sim, et al., "A simple method for in vivo labelling of infiltrating leukocytes in the mouse retina using indocyanine green dye", *Disease Models and Mechanisms*, 8(11):1479-87 (2015).

Sk, et al., "Comparative study of microtubule inhibitors—Estramustine and natural podophyllotoxin conjugated PAMAM dendrimer on glioma cell proliferation", *European Journal of Medicinal Chemistry*, 68:47-57 (2013).

Tang, et al., "Inflammation in diabetic retinopathy", *Prog. Retin. Eye Res.*, 30(5):343-58 (2011).

Teo, et al., "Preventing acute gut wall damage in infectious diarrhoeas with glycosylated dendrimers", *EMBO Mol. Med.*, 4:866-81 (2012).

Tolar, et al., "N-acetyl-L-cysteine improves outcome of advanced cerebral adrenoleukodystrophy", *Bone Marrow Transplant*, 39(4): 211-215 (2007).

Tomalia, "Starburst/Cascade Dendrimers: Fundamental building blocks for a new nanoscopic chemistry set", *Advanced Materials*, 6(7-8):529-539 (1994).

Tomalia, et al., "Starburst Dendrimers: Molecular-Level Control of Size, Shape, Surface Chemistry, Topology, and Flexibility from Atoms to Macroscopic Matter", *Chem. Int. Ed. Engl.*, 29(2):138-175 (1990).

Vandamme, et al., Poly (amidoamine) dendrimers as ophthalmic vehicles for ocular delivery of pilocarpine nitrate and tropicamide, *J. Control. Rel.*, 102:23-28 (2005).

Yiyun, et al., "Polyamidoamine dendrimers used as solubility enhancers of ketoprofen", *Eu. J. Med. Chem.*, 40:1390-3 (2005).

Zhang, et al., "Glucocorticoids: structure, signaling and molecular mechanisms in the treatment of diabetic retinopathy and diabetic macular edema", *Curr. Mol. Med.*, 14(3):376-384 (2014).

Zhang, et al., "Uniform brain tumor distribution and tumor associated macrophage targeting of systemically administered dendrimers", *Biomaterials*, 52:507-16 (2015).

Zheng, et al., "Indocyanine green-loaded biodegradable tumor targeting nanoprobes for in vitro and in vivo imaging", *Biomaterials*, 33(22):5603-9 (2012).

International Search Report for PCT application PCT/US2015/028386 dated Sep. 4, 2015.

International Search Report for PCT application PCT/US2015/045104 dated Dec. 4, 2015.

International Search Report for PCT application PCT/US2015/045112 dated Nov. 23, 2015.

International Search Report for PCT application PCT/US2016/058763 dated Feb. 3, 2017.

International Search Report for PCT application PCT/US2016/059697 dated Mar. 31, 2017.

International Search Report for PCT application PCT/US2017/016953 dated May 25, 2017.

International Search Report for corresponding PCT application PCT/US2018/029882 dated Dec. 4, 2018.

International Search Report for PCT application PCT/US2018/060795 dated Mar. 1, 2019.

Bi, et al., "Thio-lene crosslinking U polyamidoamine dendrimer-hyaluronic acid hydrogel system for biomedical applications", Journal of Biomaterials science, Polymer edition, 27(8):743-57 (2016).

Cheng, et al., "The effect of dendrimers on the pharmacodynamic and pharmacokinetic behaviors of non-covalently or covalently attached drugs", European journal of Medicinal Chemistry., 43(11) :2291-7 (2008).

Gondcaille, et al., "Phenylbutyrate up-regulates the adrenoleukodystrophy-related gene as a nonclassical peroxisome proliferator", J Cell Biol., 169(1):93-104 (2005).

Iezzi, et al., "Dendrimer-based targeted intravitreal therapy for sustained attenuation of neuroinflammation in retinal degeneration", Biomaterials, 33(3):979-988 (2012).

Kemp, et al., "Gene redundancy and pharmacological gene therapy: Implications for X-linked adrenoleukodystrophy", Nature America Inc., 4(11):1261-1268 (1998).

Nanoglue(R) Technical Data Sheet, accessed Aug. 17, 2020 (Year: 2020).

Soiberman, et al., "Subconjunctival injectable dendrimer-dexamethasone gel for the treatment of corneal inflammation", Biomaterials, 40:38-53 (2017).

Alizadeh, et al., "Tumor-associated macrophages are predominant carriers of cyclodextrin-based nanoparticles into gliomas", Nanomedicine, 6:382-90 (2010).

Lesniak, et al., "Biodistribution of fluorescently labeled PAMAM dendrimers in neonatal rabbits: effect of neuroinflammation", Mol Pharm., 10(12):4560-4571 (2013).

Van Handel, et al., "Selective uptake of multi-walled carbon nanotubes by tumor macrophages in a murine glioma model", J Neuroimmunology, 208:3-9 (2009).

Bi, et al., "Syntheisis of PAMAM dendrimer-based fast cross-linking hydrogel for biofabrication", Journal of Biomaterials Science, 26(11):669-682 (2015).

International Search Report for PCT application PCT/US2018/029882 dated Dec. 4, 2018.

Keane, et al., "Imaging chorioretinal vacular disease", Eye, 24(3):422-427 (2010).

Neal, et al., "Discovery and validation of a new class of small molecule Toll-like receptor 4 (TLR4) inhibitors ", PLoS One. 2013, 8(6): e65779 (2013).

DENDRIMER COMPOSITIONS FOR USE IN ANGIOGRAPHY

CROSS-REFERENCE TO RELATED APPLICATIONS

This application is a National Phase application under 35 U.S.C. 371 of PCT/US2018/029882, filed on Apr. 27, 2018, which claims the benefit of and priority to U.S. Provisional Application No. 62/490,936 filed Apr. 27, 2017, which are incorporated herein by reference in their entirety.

BACKGROUND

Fluorescein angiography (FA) and indocyanine green angiography (ICGA) are widely used in the context of diabetic retinopathy (DR) to verify and locate leakage, and in the context of neovascular age-related macular degeneration (AMD) to assess blood vessel heath, neovascularization, and to identify treatable lesions. While both fluorescein and indocyanine green are clinically approved, they both provide less than ideal sensitivity and signal analysis for angiography applications.

SUMMARY

In some aspects, the present disclosure provides a compound of formula (I):

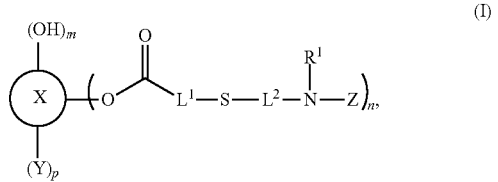

(I)

wherein, X is a G2 to G10 poly(amidoamine) (PAMAM) dendrimer; $L^1$ and $L^2$ are each independently $C_1$-$C_{12}$ alkylenyl, $C_1$-$C_{12}$ alkenylenyl, or $C_1$-$C_{12}$ alkynylenyl; Z is a fluorophore; Y is an oxidative stress probe; $R^1$ is hydrogen or alkyl; n is an integer from 1 to 100; p is an integer from 0 to 100; and m is an integer from 16 to 4000.

In other aspects, the present disclosure provides a compound of formula (I-a):

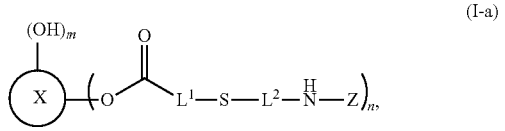

(I-a)

wherein, X is a G2 to G10 PAMAM dendrimer; $L^1$ and $L^2$ are each independently $C_1$-$C_{12}$ alkylenyl, $C_1$-$C_{12}$ alkenylenyl, or $C_1$-$C_{12}$ alkynylenyl; Z is a fluorophore; n is an integer from 1 to 100; and m is an integer from 16 to 4000.

In certain aspects, the present disclosure provides a compound of formula (I-b):

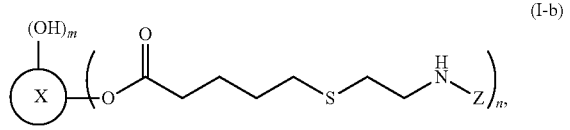

(I-b)

wherein, X is a G2 to G10 PAMAM dendrimer; Z is a fluorophore; n is an integer from 1 to 100; and m is an integer from 16 to 4000.

In other aspects, the present disclosure provides a method for performing angiography on a subject in need thereof, the method comprising administering a composition to the subject, the composition comprising the dendrimer of formulas (I), (I-a) and/or (I-b); and observing and/or quantifying the fluorescence emitted in the subject's eye vasculature.

In other aspects, the present disclosure provides pharmaceutical compositions and kits that include the dendrimer of formulas (I), (I-a) and/or (I-b).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
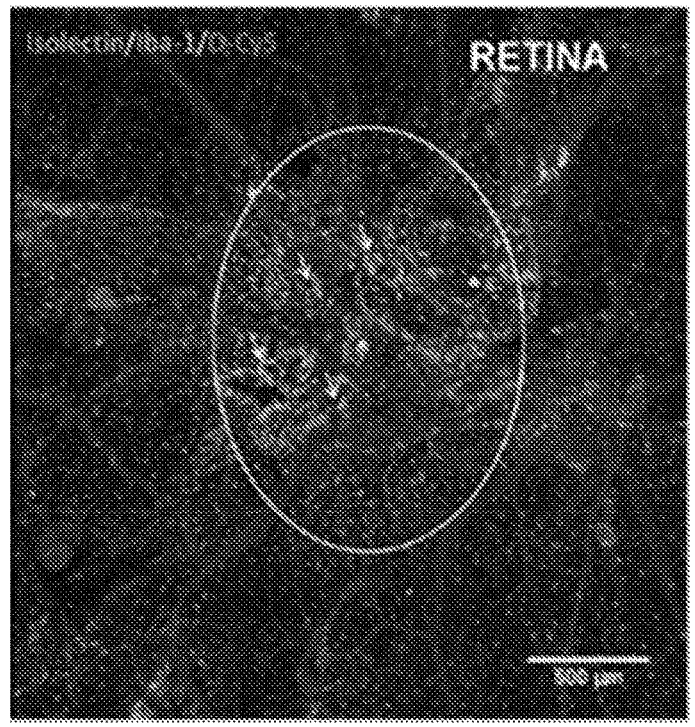
Figure 1B:
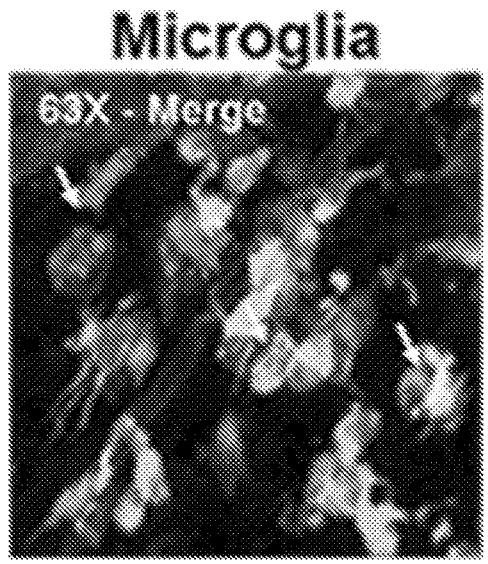
Figure 1C:
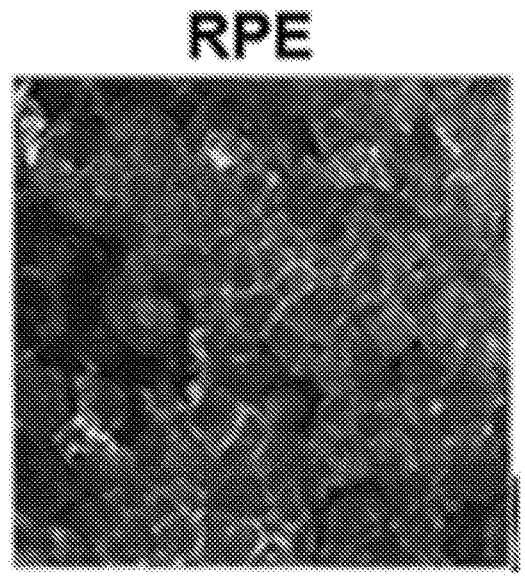

Having thus described the presently disclosed subject matter in general terms, reference will now be made to the accompanying Figures, which are not necessarily drawn to scale, and wherein:

FIG. 1A, FIG. 1B, and FIG. 1C show confocal images of rat retinal flat mount in rat model of choroidal neovascularization following administration of dendrimer-Cy®5 (D-Cy5). FIG. 1A shows a merge of confocal images of the retina. FIG. 1B shows a merge of confocal images of microglia. FIG. 1C shows a merge of confocal images of retinal pigment epithelium (RPE). D-Cy5: red; microglia/macrophages: green; lectin; blue; white circle: area of inflammation; and white arrow: co-localization. Scale bar is 500 μm.

Figure 2:
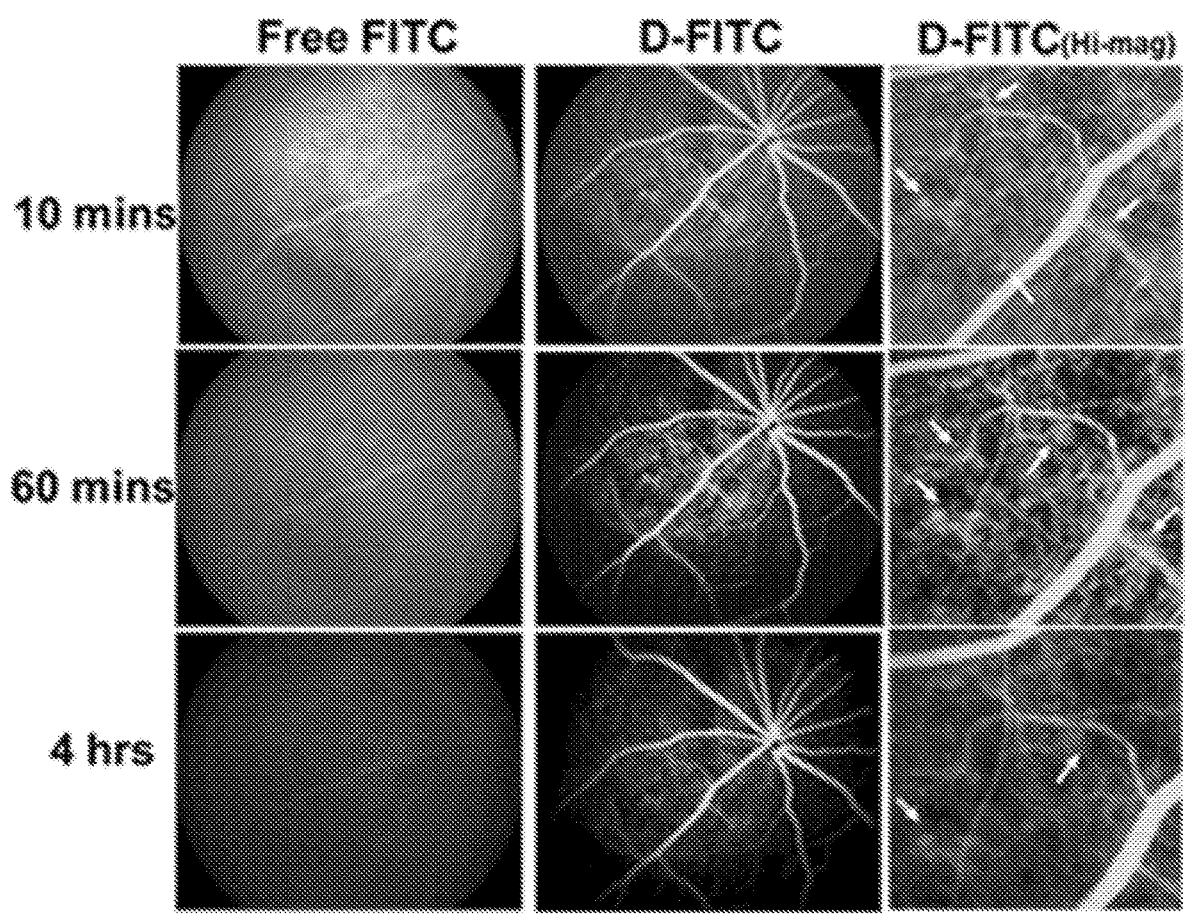

FIG. 2 shows fundus fluorescence angiogram analysis for free-FITC and dendrimer-FITC (D-FITC) at different time points (10 min, 60 min and 4 hrs) after injection. White arrows indicate precise location of retinal leakage identified by D-FITC nanoparticles.

DETAILED DESCRIPTION

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Compounds, Compositions, and Methods for Performing Angiography

Blood-retinal barrier (BRB) dysfunction/retinal vascular permeability leading to macular edema is a major contributor to visual loss in AMD and DR. The central mechanism of BRB dysfunction is an alteration in the permeability of retinal vascular endothelial cells. Pro-inflammatory changes play a major role in this mechanism and the pathogenesis of DR, as shown in animal models and patients. Systemic targeting of ocular inflammation may provide opportunities to address this challenge.

Dendrimers (e.g., globular, nanostructured polymers) are emerging as promising candidates for targeted drug and gene delivery. The small size, and high density of tailorable surface functional groups may provide significant advantages in ocular applications. PAMAM dendrimers disclosed herein are nontoxic, and can be cleared intact through the kidney or liver depending on size. The disclosed dendrimers, with no targeting ligands, can selectively localize in cells associated with neuroinflammation in the retina and the brain. For example, in a rat CNV model, the disclosed dendrimers were able to target choroidal and retinal inflammation. The disclosed dendrimers have the potential for clinical translation. Accordingly, the use of ICG (which is approved for humans), in conjunction with the dendrimers, may enable easier approval for the disclosed dendrimer-ICG conjugates for imaging/diagnosis.

This disclosure describes novel ways (a) to image abnormal blood vessels in the eye (angiography), (b) to image/ quantify longitudinal measurements of cell-specific inflammation and oxidative stress, and (c) to provide methods for image-guided therapies. The fluorophore labeled dendrimer, when administered intravenously, can leak specifically into the disease-affected parts of the eye, providing a significantly-increased contrast and sensitivity to angiography. This characteristic can ultimately enable better regional identification of the neovascular area, compared to the current state-of-the art (e.g., free ICG and fluorescein). As such, the ability of the dendrimer to localize into the affected areas involved in neovascularization can be used to improve angiography and image-guided therapy approaches.

A. Dendrimers of Formula (I)

The term "dendrimer" refers to repeatedly branched nano-sized macromolecules characterized by a symmetrical (and in some embodiments non-symmetrical), well-defined three-dimensional shape. Dendrimers grow three-dimensionally by the addition of shells of branched molecules to a central core. The cores are spacious and various chemical units can be attached to points on the exterior of the central core. Dendrimers have been described extensively (Tomalia. (1994). *Advanced Materials* 6:529-539; Donald A. Tomalia, Adel M. Naylor, William A. Goddard III (1990). Angew, *Chem. Int. Ed. Engl.*, 29:138-175; incorporated herein by reference in their entireties). Dendrimers can be synthesized as spherical structures typically ranging from 1 to 20 nanometers in diameter. In certain embodiments, the dendrimers provided herein have a diameter of from about 1 nm to about 20 nm, such as from about 1 nm to about 8 nm or from about 12 nm to about 20 nm. In certain embodiments, the dendrimer has a diameter of less than or equal to 20 nm, less than or equal to 19 nm, less than or equal to 18 nm, less than or equal to 17 nm, less than or equal to 16 nm, or less than or equal to 15 nm. Diameter may be measured by methods known within the art, such as (but not limited to) dynamic light scattering and electron microscopy.

Dendrimers are identified by a generation number (Gn) and each complete synthesis reaction results in a new dendrimer generation. Molecular weight and the number of terminal (e.g., surface) groups increase exponentially as a function of generation number (e.g., the number of layers) of the dendrimer. Further description of dendrimers can be found in U.S. Pat. No. 9,345,781, WO WO2009/046446, and U.S. Patent Application Publication No. 2017/0043027, all of which are incorporated by reference herein in their entirety.

As used herein, the term "PAMAM dendrimer" refers to poly(amidoamine) dendrimer, which may contain different cores, with amidoamine building blocks. The method for making them is known to those of skill in the art and generally, involves a two-step iterative reaction sequence that produces concentric shells (generations) of dendritic β-alanine units around a central initiator core. This PAMAM core-shell architecture grows linearly in diameter as a function of added shells (generations). Meanwhile, the surface groups amplify exponentially at each generation according to dendritic-branching mathematics. An exemplary surface group for the disclosed dendrimers is a —OH group, which, e.g., is depicted below in formulas (I), (I-a) and (I-b). The dendrimers can be generations G1-10 with 5 different core types and 10 functional surface groups. The dendrimer may be of G2 to G10 in range, such as G2 to G6 or G4 to G5, with mixtures of different G levels also possible. In certain embodiments, the PAMAM dendrimer is a G4 dendrimer with hydroxyl surface groups. In certain embodiments, the dendrimer does not include a targeting ligand, such as an aptamer, antibody or protein (or fragments thereof).

In certain embodiments, the presently disclosed subject matter provides dendrimers of Formula (I):

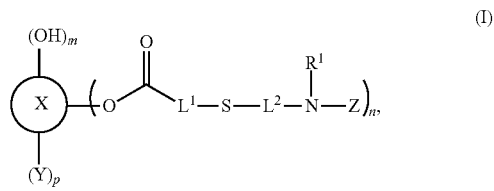

wherein, X is a G2 to G10 poly(amidoamine) (PAMAM) dendrimer; $L^1$ and $L^2$ are each independently $C_1$-$C_{12}$ alkylenyl, $C_1$-$C_{12}$ alkenylenyl, or $C_1$-$C_{12}$ alkynylenyl; Z is a fluorophore; Y is an oxidative stress probe; $R^1$ is hydrogen or alkyl; n is 1 to 100; p is 0 to 100; and m is 16 to 4000.

The dendrimers disclosed herein include a fluorophore. The fluorophore can be covalently linked through the terminal ends of the PAMAM dendrimer, e.g., through the multitude of hydroxyl groups present on the dendrimers surface. This type of bond is depicted in formulas (I), (I-a) and (I-b) as an ester bond covalently attached to the dendrimer. In certain embodiments, about 0.1% to about 20% of the terminal groups of the dendrimer are covalently linked to a fluorophore, such as from about 1% to about 20%, from about 1% to about 10%, or from about 0.1% to about 5%.

The combination of the hydroxyl-terminated PAMAM dendrimer and the inclusion of a fluorophore allow the disclosed dendrimers to be useful for angiography applications, and in particular retinal angiography. Any suitable fluorophore can be used in the dendrimers disclosed herein, as long as it still provides useful dendrimers for angiography applications. Examples of fluorophores include, but are not limited to, indocyanine green, fluorescein (e.g., fluorescein isocyanate), boron-dipyrromethene, rhodamine, and rose Bengal. These dyes can be used for various ophthalmic imaging purposes such as fluorescence angiography and grading corneal inflammation (particularly in dry eye). The dendrimer can include more than one fluorophore and can include more than one type of fluorophore. In certain embodiments, the dendrimer includes a fluorophore (e.g., Z) selected from the group consisting of:

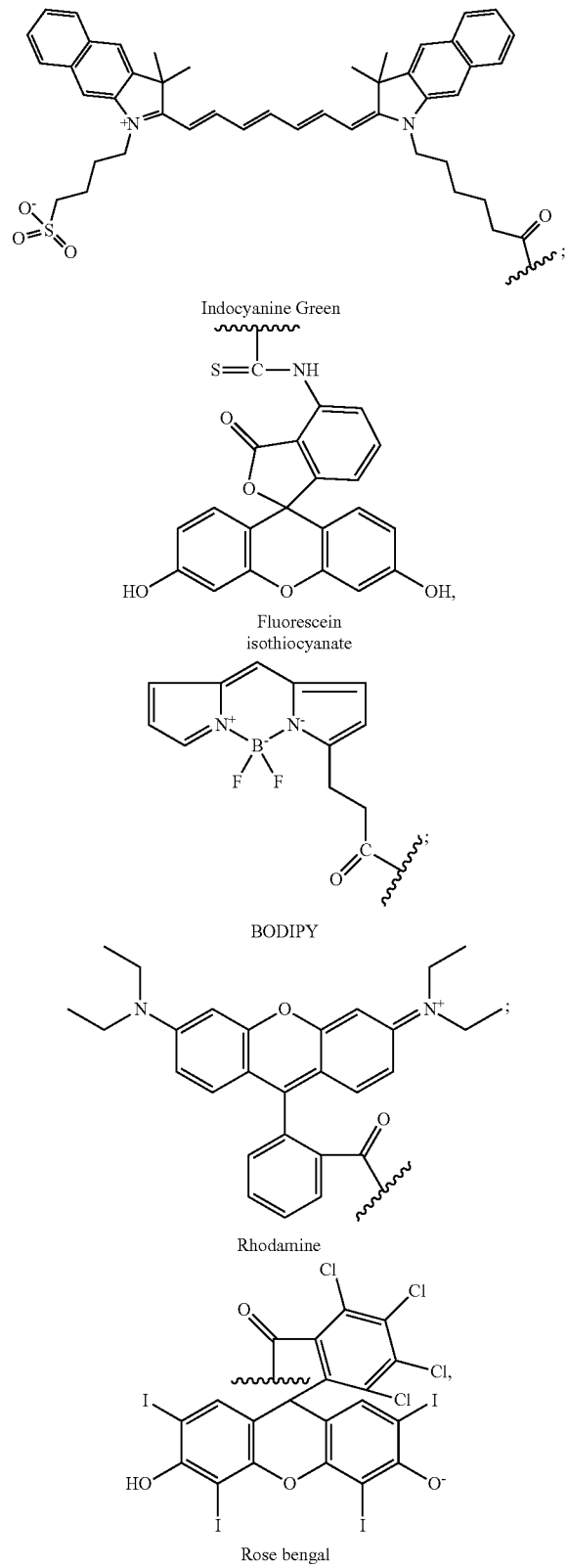

and a combination thereof.

The dendrimer may include an oxidative stress probe. As used herein, the term "oxidative stress probe" refers to fluorescent agents that can fluoresce due to the presence of oxidative stress. For example, an oxidative stress probe may refer to a fluorescent agent that can fluoresce due to oxidative stress caused by the presence of reactive oxygen species, such as peroxides (e.g., hydrogen peroxide), superoxide, hydroxyl radical and/or singlet oxygen. Since oxidative stress is pronounced in inflammatory cells, imaging these areas at later time-points may provide clinicians useful information regarding the stage of the disease, and/or exact locations of where potential neovascularization can develop. This information may help clinicians to direct laser treatment for photocoagulation or photodynamic therapy. Accordingly, by attaching the appropriate imaging agent (for assessing the cellular level inflammation and oxidative stress) to the dendrimer, eye vasculature (e.g., retina, choroid, and the like) can be longitudinally imaged and quantified in disease progression. In addition, by attaching photosensitive- or radiation-sensitive agents to the dendrimer, specific cells can be manipulated through external stimulation (e.g., radiation, photodynamic therapies). Many oxidative stress probes have been identified, including but not limited to, 4-nitrotyrosine, malonaldehyde, 8-isoprostane, 7-ethyl-10-hydroxycamptothecin, 4-hydroxy-2-nonenal, and the like, which can fluoresce in the presence of $H_2O_2$ in cells that are under oxidative stress. These dyes can be conjugated to the dendrimer surface covalently (e.g., through hydroxyl groups) as an additional probe for imaging inflammation and oxidative stress via fluorescence angiography. The dendrimer can include more than one oxidative stress probe and can include more than one type of oxidative stress probe. In certain embodiments, the oxidative stress probe (e.g., Y) is selected from the group consisting of 7-ethyl-10-hydroxycamptothecin, 4-hydroxy-2-nonenal, nitrotyrosine, 8-hydroxy-2'-deoxyguanosine, malonaldehyde, 8-isoprostane, and a combination thereof.

In certain embodiments of the dendrimer of formula (I), X is a G2 to G6 PAMAM dendrimer; $L^1$ and $L^2$ are each independently $C_1$-$C_6$ alkylenyl, $C_1$-$C_6$ alkenylenyl, or $C_1$-$C_6$ alkynylenyl; n is an integer from 1 to 10; p is an integer from 1 to 10; and m is an integer from 1 to 250.

In certain embodiments of the dendrimer of formula (I), $L^1$ and $L^2$ are each independently $C_1$-$C_6$ alkylenyl; n is an integer from 1 to 5; and p is an integer from 1 to 5.

In certain embodiments, the dendrimer has formula (I-a):

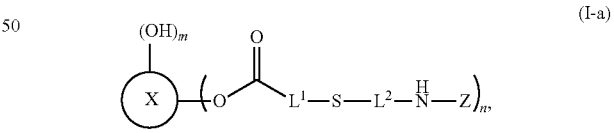

(I-a)

wherein, X is a G2 to G10 PAMAM dendrimer; $L^1$ and $L^2$ are each independently $C_1$-$C_{12}$ alkylenyl, $C_1$-$C_{12}$ alkenylenyl, or $C_1$-$C_{12}$ alkynylenyl; Z is a fluorophore; n is an integer from 1 to 100; and m is an integer from 16 to 4000.

In certain embodiments of the dendrimer of formula (I-a), X is a G2 to G6 PAMAM dendrimer; $L^1$ and $L^2$ are each independently $C_1$-$C_6$ alkylenyl, $C_1$-$C_6$ alkenylenyl, or $C_1$-$C_6$ alkynylenyl; n is an integer from 1 to 10; and m is an integer from 1 to 250.

In certain embodiments of the dendrimer of formula (I-a), $L^1$ and $L^2$ are each independently $C_1$-$C_6$ alkylenyl; and n is an integer from 1 to 5.

In certain embodiments, the dendrimer has formula (I-b):

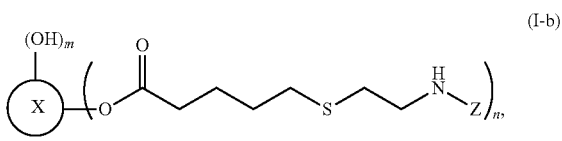

wherein, X is a G2 to G10 PAMAM dendrimer; Z is a fluorophore; n is an integer from 1 to 100; and m is an integer from 16 to 4000.

In certain embodiments of the dendrimer of formula (I-b), X is a G2 to G6 PAMAM dendrimer; n is an integer from 1 to 10; and m is an integer from 1 to 250.

In certain embodiments of the dendrimer of formulas (I), (I-a), and/or (I-b), X is a G4 PAMAM dendrimer; n is 2; and m is 62.

In certain embodiments, the dendrimer of formulas (I), (I-a), and/or (I-b) is selected from the group consisting of:

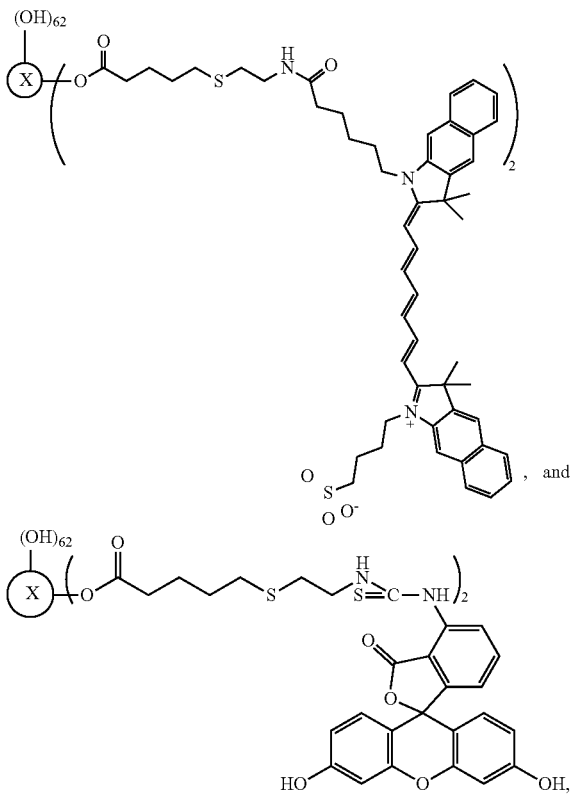

wherein X is a G4 PAMAM dendrimer.

B. Methods of Performing Angiography

In another aspect, disclosed are methods of performing angiography, and in particular retinal angiography. Retinal angiography is a technique that can be used for examining the eye vasculature, such as the circulation of the retina and choroid (e.g., parts of the fundus) using a fluorescent dye and typically a specialized angiographic camera. Retinal angiography involves the administration of the fluorescent dye into the systemic circulation of a subject, and then analyzing the fluorescence emitted from the observed region (e.g., retina). In certain embodiments, analysis can be done by obtaining an angiogram via the specialized angiographic camera.

Angiography is used widely in DME to verify and locate leakage, and in other situations to assess blood vessel heath and treatable lesions. Fluorescein and ICG are used in DME and AMD to verify leakage and provide insights into the location of the leakage, and in other situations to assess blood vessel heath and treatable lesions. At typical intravenous doses of approximately 10 mg/kg of the dyes, they are associated with side effects including nausea and low blood pressure, and can interact with other drugs. Both fluorescein and ICG are metabolized either hepatically or renally, which is not ideal for imaging agents.

As detailed above, current methods rely on fluorescein and ICG dyes, which have associated drawbacks (quick clearance, low sensitivity, and the like). The disclosed dendrimers having a covalently linked fluorophore may be able to overcome the problems associated with the aforementioned free dyes by: 1) being selective to the diseased/injured area(s), so that the affected areas can be clearly delineated; 2) provide enhanced contrast (relative to the free dye); and 3) improve sensitivity which may allow quantification of the differences in the extent of different eye diseases (e.g., DR or AMD) between different patients. Due to the advantages of the dendrimers, they may provide valuable insights into the spatial pro-inflammatory distribution across a large area, even far from the leaky vessels, as well as insights into the extent of inflammation, longitudinally, thereby being used to monitor the response to a therapy. They also may be analyzed and quantified across different regions of the retina, providing valuable insights into the differential local inflammation, edema, vessel impairment, and/or microaneurysms.

The disclosed methods of performing angiography on a subject (in need thereof) include administering a composition to the subject, wherein the composition comprises a dendrimer as disclosed herein. The method further includes observing and/or quantifying the fluorescence emitted in the subject's eye vasculature. In certain embodiments, the method includes observing and/or quantifying the fluorescence emitted in the subject's eye retina, choroid, or both.

In certain embodiments, the composition comprises a hydroxyl-terminated poly(amidoamine) (PAMAM) dendrimer covalently linked to a fluorophore. In certain embodiments, the fluorophore comprises indocyanine green, fluorescein or a combination thereof. In certain embodiments, the composition comprises the dendrimer having formula (I), (I-a) and/or (I-b) as described above.

The composition may include dendrimers of varying diameters, which may localize to distinct vasculature location due in part to their size. The composition may include 2, 3, or 4 different sets of dendrimers, each independently having a specific diameter size range. For example, the composition may include a first set of dendrimers having a size of from about 1 nm to about 8 nm, including 1, 2, 3, 4, 5, 6, 7, and 8 nm, and a second set of dendrimers having a size of from about 12 nm to about 20 nm, including 12, 13, 14, 15, 16, 17, 18, 19, and 20 nm. In addition, the composition may include dendrimers having varying fluorophores bound thereto. For example, the composition may include a first set of dendrimers having one size and having a first fluorophore and a second set of dendrimers having a different size from the first set and having a second fluorophore, which is also different from the first fluorophore. Accordingly, at least size and bound fluorophore of the dendrimer may be used to provide more detailed information of the eye vasculature during angiography.

The composition may include other components in addition to the dendrimer. For example, the composition may further include a pharmaceutically acceptable carrier, such as those described below. In certain embodiments, the composition is a pharmaceutical composition as described below.

The composition may be administered at varying times depending on subject, disease, etc. For example, the composition may be administered 1 to 4 times daily for a period of 28 days, at any suitable interval. The composition may also be administered 1 to 10 times (total) over a period of 28 days, at any suitable interval that can allow for an accurate analysis of the subject. Starting from the administration of the composition, the method may be performed over a period of about 10 seconds to about 28 days, such as from about 10 seconds to about 21 days, from about 10 seconds to about 1 hour, from about 1 minute to about 30 minutes, or from about 1 day to about 21 days. In certain embodiments, the method includes a single administration of the composition and is performed for at least 21 days. During the time frame that the method is being performed, the step of observing and/or quantifying the fluorescence emitted in the subject's retina can be performed any suitable number of times. For example, in embodiments that the method is performed for at least 21 days, the step of observing and/or quantifying the fluorescence emitted in the subject's retina can be performed once daily, twice daily, once every 2 days, once every 3 days, etc.

The composition may be administered at varying dosages depending on the subject, disease, etc. The composition may be administered at a dosage of from about 0.1 mg/kg to about 20 mg/kg, such as from about 1 mg/kg to about 15 mg/kg, or from about 5 mg/kg to about 10 mg/kg. In certain embodiments, the composition is administered at a dosage of less than or equal to 20 mg/kg, less than or equal to 18 mg/kg, less than or equal to 16 mg/kg, less than or equal to 14 mg/kg, less than or equal to 12 mg/kg, less than or equal to 10 mg/kg, less than or equal to 8 mg/kg, less than or equal to 6 mg/kg, or less than or equal to 4 mg/kg. In certain embodiments, the composition may be administered at a dosage of greater than or equal to 0.1 mg/kg, greater than or equal to 1 mg/kg, greater than or equal to 2 mg/kg, greater than or equal to 4 mg/kg, greater than or equal to 6 mg/kg, greater than or equal to 8 mg/kg, or greater than or equal to 10 mg/kg.

Retinal angiography can be used to analyze eye vasculature (e.g., blood barrier integrity) in a number of eye diseases. Blood barrier dysfunction in a subject can be detected and quantified by observing the escape of dendrimers from blood vessels of the subject. The dendrimers permit detection and diagnosis of the extent of blood barrier dysfunction. Thus, the type and, in some embodiments, the concentration of label detected outside the blood barrier facilitates such diagnosis.

To quantify such dysfunction, numerical values can be assigned based on the fluorescence analyzed in the eye vasculature. For example, if essentially no dendrimers escape is detected, the blood barrier can be identified as having a grade 0 or no dysfunction blood barrier. If very small dendrimers or very small amount of dendrimers escape from blood vessels, the blood barrier can be identified as having a grade 1 or mildly dysfunctional blood barrier. If slightly larger dendrimers or slightly larger amount of dendrimers escape from blood vessels, the blood barrier can be identified as having a grade 2 or moderately dysfunctional blood barrier. If somewhat larger dendrimers or somewhat larger amount of dendrimers escape from blood vessels, the blood barrier can be identified as having a grade 3 or somewhat severely dysfunctional blood barrier.

If even larger dendrimers or even larger amount of dendrimers escape from blood vessels, the blood barrier can be identified as having a grade 4 or very severely dysfunctional blood barrier, and so forth.

Examples of blood barrier dysfunction (in the eye) include, but are not limited to, diabetic retinopathy, macular degeneration, cytomegalovirus (CMV) eye infection, retinitis, choroidal ischemia, acute sectorial choroidal ischemia, and ischemic optic neuropathy. For example, in certain embodiments, the subject has age-related macular degeneration (AMD), retinitis pigmentosa, optic neuritis, infection (e.g., CMV infection), uveitis, sarcoid, sickle cell disease, retinal detachment, temporal arteritis, retinal ischemia, choroidal ischemia, choroidal ischemia, ischemic optic neuropathy, arteriosclerotic retinopathy, hypertensive retinopathy, retinal artery blockage, retinal vein blockage, hypotension, diabetic retinopathy, macular edema, choroidal neovascularization, or a combination thereof. In certain embodiments, the subject has AMD and/or diabetic retinopathy.

Accordingly, the dendrimers and methods disclosed herein may be used to identify diseased vasculature in the retina, including inflamed and/or leaky (e.g., edema) vasculature. In addition, the dendrimers and methods may be able to identify at which stage the above-listed diseases are. As mentioned above, dendrimers that include an oxidative stress marker can be observed and/or quantified at longitudinal time-points, and may be able to provide clinicians more profound information regarding the stage of the disease and/or exact locations of potential neovascularization development. For example, the method may include identifying whether the subject has an eye disease at early stage or late stage.

The method also may be combined with other methods known within the art used to characterize the vasculature of the eye, such as Optical Coherence Tomography (OCT). For example, the method may further comprise performing OCT on the subject.

The identification and characterization of disease state provided by the methods may allow for clinicians to then identify a subject in need of treatment thereof. For example, the method may further comprise identifying the subject as having a disease, thereby identifying the subject as in need of treatment thereof said disease. As such, the method may further comprise identifying the subject as in need of treatment for an eye disease. In addition, the method may further comprise administering to the subject (identified as in need of treatment of an eye disease) an effective amount of a therapeutic agent to said subject.

The therapeutic agent may be any suitable agent that ameliorates the above identified diseases. A therapeutic agent may decrease, suppress, attenuate, diminish, arrest, or stabilize the development or progression of disease, disorder, or condition in a host organism. For example, the therapeutic agent may be an agent that can treat inflammatory and/or angiogenic diseases, or an oxidative stress related disease. Non-limiting examples of therapeutic agents that can be used in the methods of the present disclosure include drugs in the non-steroidal anti-inflammatory drug class (NSAID). Examples of NSAIDS used in the methods of the present invention include mefenamic acid, aspirin, Diflunisal, Salsalate, Ibuprofen, Naproxen, Fenoprofen, Ketoprofen, Deacketoprofen, Flurbiprofen, Oxaprozin, Loxoprofen, Indomethacin, Sulindac, Etodolac, Ketorolac, Diclofenac, Nabumetone, Piroxicam, Meloxicam, Tenoxicam, Droxicam, Lornoxicam, Isoxicam, Meclofenamic acid, Flufenamic acid, Tolfenamic acid, elecoxib, Rofecoxib, Valdecoxib, Parecoxib, Lumiracoxib, Etoricoxib, Firocoxib, Sulphonanilides, Nimesulide, Niflumic acid, and Licofelone. Other anti-inflammatory agents include steroids, such as methyl prednisone, dexamethasone, non-steroidal anti-inflammatory agents, including COX-2 inhibitors, corticosteroid anti-inflammatory agents, gold compound anti-inflammatory agents, immunosuppressive anti-inflammatory and anti-angiogenic agents, salicylate anti-inflammatory agents, ranibizumab, minocycline, anti-VEGF agents, including aflibercept, and rapamycin. The therapeutic agent may also include antibodies, such as daclizumab, bevacizumab (Avastin®), ranibizumab) (Lucentis®), basiliximab, ranibizumab, and pegaptanib sodium or peptides like SN50, and antagonists of NFκβ. In addition, the therapeutic agent may include anti-oxidants such as N-acetyl cysteine, omega-3 fatty acid derivatives such as resolving and neuroprotectin-D1 (NPD1).

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition (e.g., a disease, condition, or disorder related the vasculature of the eye), or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The term "administering" as used herein refers to contacting a subject with the composition comprising the disclosed dendrimers. The composition can be administered using a variety of methods known in the art depending on the subject and the particular disease, disorder, or condition being investigated The administering can be carried out by, for example, intravenous infusion; injection by intravenous, intraperitoneal, intramuscular, intraocular, or intraarterial. In certain embodiments, administering the composition includes injecting the composition intravenously into the vasculature of the subject.

The administration of the composition may be a systemic administration. The phrase "systemic administration," and "administered systemically" as used herein refers to the administration of a compound, drug or other material other than directly into the eye vasculature, such that it enters the patient's system and, thus, is subject to metabolism and other like processes, for example, subcutaneous administration.

The subject of disclosed methods in their many embodiments is desirably a human subject, although it is to be understood that the methods described herein are effective with respect to all vertebrate species, which are intended to be included in the term "subject." Accordingly, a "subject" can include a human subject for medical purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein.

C. Pharmaceutical Compositions

In another aspect, disclosed are pharmaceutical compositions of dendrimers of formula (I), (I-a) and/or (I-b) in admixture with a pharmaceutical acceptable carrier. The pharmaceutical compositions can be administered to a subject, for example, a human subject, in the methods of performing angiography disclosed herein. As used herein, "pharmaceutical acceptable carrier" refers to a physiologically acceptable diluent including, but not limited to water, phosphate buffered saline, or saline, and, in certain embodiments, can include an adjuvant. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG.

Compositions to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

The disclosed pharmaceutical compositions can be manufactured in a manner known in the art, e.g. by means of conventional mixing, dissolving, granulating, dragee-making, levitating, emulsifying, encapsulating, entrapping or lyophilizing processes.

Pharmaceutical compositions for systemic administration include aqueous solutions of the dendrimer. For injection, the presently disclosed pharmaceutical compositions can be formulated in aqueous solutions, for example, in some embodiments, in physiologically compatible buffers, such as Hank's solution, Ringer' solution, or physiologically buffered saline. Aqueous injection suspensions can contain substances that increase the viscosity of the suspension, such as sodium carboxymethyl cellulose, sorbitol, or dextran. Additionally, suspensions of the dendrimer can include fatty oils, such as sesame oil, or synthetic fatty acid esters, such as ethyl oleate or triglycerides, or liposomes. Optionally, the suspension also can contain suitable stabilizers or agents that increase the solubility of the compounds to allow for the preparation of highly concentrated solutions.

In some embodiments, the pharmaceutical composition can be a lyophilized powder, optionally including additives, such as 1 mM-50 mM histidine, 0.1%-2% sucrose, 2%-7% mannitol at a pH range of 4.5 to 5.5 that is combined with buffer prior to use.

Actual dosage levels of the dendrimer in the presently disclosed pharmaceutical compositions can be varied so as to obtain an amount of the dendrimer that is effective to achieve the desired characterization of particular subject's retina, without being toxic to the subject. The selected dosage level will depend on a variety of factors including the activity of the particular dendrimer employed, the route of administration, the time of administration, the rate of excretion of the particular dendrimer being employed, the duration of the treatment, other drugs, compounds and/or materials used in combination with the particular dendrimer employed, the age, sex, weight, condition, general health and prior medical history of the subject being treated, and like factors well known in the medical arts.

A physician or veterinarian having ordinary skill in the art can readily determine and prescribe the amount of the pharmaceutical composition required for performing angiography. For example, the physician or veterinarian could start doses of the dendrimers of formula (I), (I-a) and/or (I-b) employed in the pharmaceutical composition at levels lower than that required to achieve the desired effect and gradually increase the dosage until the desired effect is achieved. Accordingly, the dosage range for administration will be adjusted by the physician as necessary. It will be appreciated that an amount of a compound required for achieving the desired angiography analysis in one disease, may be different from the amount of dendrimer needed for another disease.

In general, the dosages and administration regimens listed above in reference to the methods of performing angiography can also be applied to the pharmaceutical compositions.

D. Kits

The presently disclosed dendrimers and pharmaceutical compositions can be assembled into kits for use in angiography methods, and in particular retinal angiography. In certain embodiments, the presently disclosed kits include a pharmaceutical composition that includes a dendrimer of formula (I), (I-a), and/or (I-b). In particular embodiments, the dendrimers of formula (I), (I-a), and/or (I-b) are in unit dosage form. In further embodiments, the dendrimer of formula (I), (I-a), and/or (I-b) can be present together with a pharmaceutically acceptable solvent, carrier, excipient, or the like, as described herein.

In certain embodiments, the disclosed kits comprise one or more containers, including, but not limited to a vial, tube, ampule, bottle and the like, for containing the pharmaceutical composition including the dendrimer or the dendrimer. The dendrimer may be present solvated, in suspension, or powder form. The dendrimer may then be reconstituted in the pharmaceutically acceptable carrier to provide the pharmaceutical composition. The one or more containers also can be carried within a suitable carrier, such as a box, carton, tube or the like. Such containers can be made of plastic, glass, laminated paper, metal foil, or other materials suitable for holding medicaments.

In certain embodiments, the container can hold a pharmaceutical composition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The disclosed kits also can include associated instructions for using the dendrimers and pharmaceutical compositions for performing angiography, in particular retinal angiography. In certain embodiments, the instructions include one or more of the following: a description of the dendrimer; a dosage schedule and administration for performing retinal angiography; precautions; warnings; indications; counter-indications; overdosage information; adverse reactions; animal pharmacology; clinical studies; and references. The instructions can be printed directly on a container (when present), as a label applied to the container, as a separate sheet, pamphlet, card, or folder supplied in or with the container.

E. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "alkyl" as used herein, means a straight or branched, saturated hydrocarbon chain containing from 1 to 10 carbon atoms, including 1, 2, 3, 4, 5, 6, 7, 8, 9, and 10 carbon atoms. The term "lower alkyl" or "$C_1$-$C_6$-alkyl" means a straight or branched chain hydrocarbon containing from 1 to 6 carbon atoms, including 1, 2, 3, 4, 5, and 6 carbon atoms. The term "$C_1$-$C_3$-alkyl" means a straight or branched chain hydrocarbon containing from 1 to 3 carbon atoms, including 1, 2, and 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylenyl," as used herein, refers to a divalent group derived from a straight or branched chain hydrocarbon of 1 to 50 carbon atoms, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, for example, of 1 to 5 carbon atoms, including 1, 2, 3, 4, and 5 carbon atoms. Representative examples of alkylenyl include, but are not limited to, —$CH_2$—, —$CH_2$—$CH_2$—, —$CH_2$—$CH_2$—$CH_2$—, —$CH_2$—$CH_2$—$CH_2$—$CH_2$—, and —$CH_2$—$CH_2$—$CH_2$—$CH_2$—$CH_2$—.

The term "alkenylenyl," as used herein, refers to a divalent group derived from a straight or branched chain hydrocarbon of 2 to 50 carbon atoms, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 carbon atoms, wherein at least one carbon-carbon bond is a double bond. Representative examples of alkenylenyl include, but are not limited to, —CH=CH—, —CH=CH—$CH_2$—, —$CH_2$—CH=CH—$CH_2$—, and —$CH_2$$CH_2$—CH=CH—$CH_2$—.

The term "alkynylenyl," as used herein, refers to a divalent group derived from a straight or branched chain hydrocarbon of 2 to 50 carbon atoms, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 carbon atoms, wherein at least one carbon-carbon bond is a triple bond. Representative examples of alkynylenyl include, but are not limited to, —C≡C—, —C≡C—CH$_2$—, —C≡C—CH$_2$—CH$_2$— and —CH$_2$—C≡C—CH$_2$—.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The symbol ($\sim\!\sim\!\sim$) denotes the point of attachment of a moiety to the remainder of the molecule.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of Dendrimer-Fluorescent Probes

D-ICG conjugates were synthesized using thiol-ene click chemistry. The conjugates were synthesized using a 2 step reaction process (see Scheme 1). In the first step, a bifunctional dendrimer was synthesized using esterification reaction resulting in partial modification of the dendrimer surface with 2 to 3 primary amine (e.g., —NH$_2$) groups. In the second step, indocynine green (ICG) was reacted to the dendrimer surface using a click reaction forming D-ICG conjugates. The conjugates were purified using dialysis and characterized using $^1$H-NMR, which confirmed the formation of conjugates. HPLC characterization confirmed that the conjugates are pure. Fluorescence spectroscopy characterization confirmed that the fluorescence of D-ICG was similar to that of free ICG.

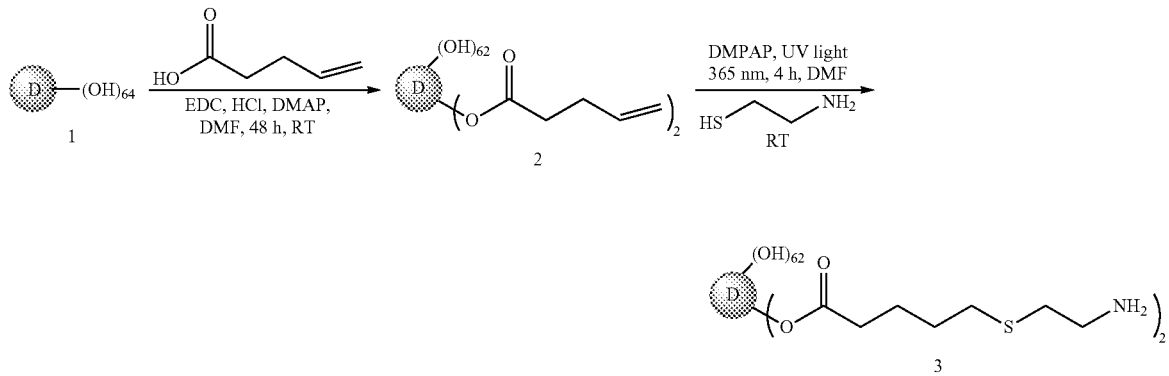

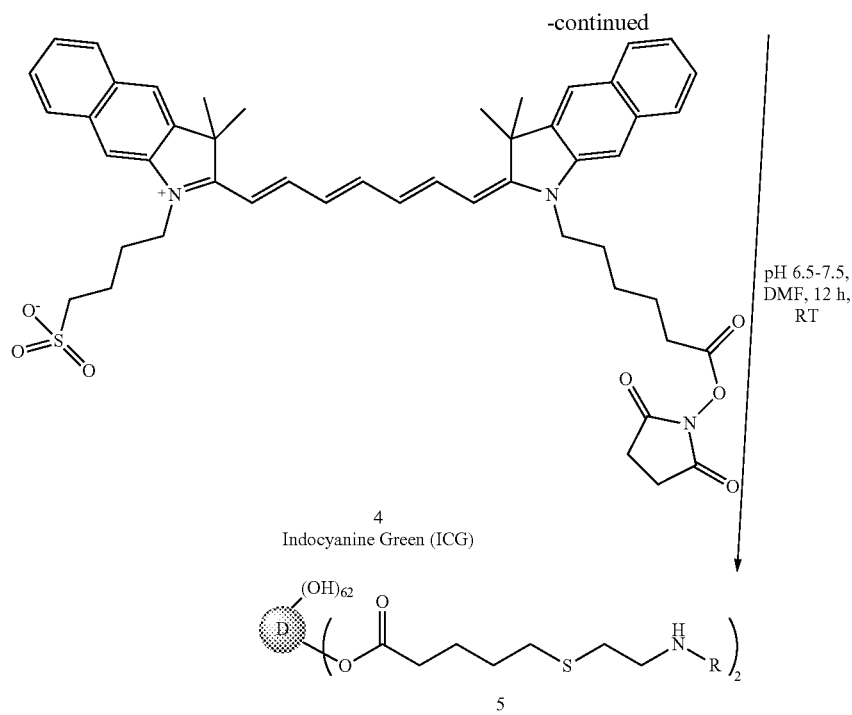

4
Indocyanine Green (ICG)

Other dendrimer-fluorescent probes can be synthesized using Scheme 1, as listed above. For example, Cy5-labeled dendrimer and FITC-labeled dendrimer may be synthesized by similar methods as listed above.

Example 2

Use of Dendrimer-Fluorescent Probes in Choroidal Neovascularization (CNV) Rat Model In this model, subretinal injection of a lipid was performed to experimentally induce CNV, and was associated with significant inflammation and oxidative stress. On day 3 (post-lipid injection) Cy5-labeled dendrimer (D-Cy5) was intravenously administered to the rats. The macrophage activation and D-Cy5 localization were imaged 7 days after dendrimer administration (e.g., Day 10). In the CNV area, there was a significant increase in macrophages compared to healthy control eyes. These studies suggest that: (1) the disclosed dendrimers selectively localize in the CNV region, in activated microglia/macrophages (mi/ma), and are retained for at least 21 days. (2) Minimal uptake is seen in the mi/ma, in the control healthy eyes. Systemic dendrimer therapy with dendrimer-N-Acetyl cysteine (D-NAC) conjugates (20 mg/kg) resulted in an approximately 78% reduction in CNV, and an approximately 63% reduction in macrophage accumulation by significantly suppressing inflammatory cytokines (TNF-α, IL-1β, IL-6, MCP-1) compared to free NAC and PBS treated controls.

The localization of D-Cy5 in the retina can be seen in FIG. 1. More particularly, FIG. 1 shows confocal images of rat retinal flat mount with subretinal lipid on day 0 and D-Cy5 that were administrated systemically on day 3 and imaged on day 10. D-Cy5 (red) were found co-localized in activated microglia (green, white arrows) and hypertrophic RPE in the areas of inflammation (white circle). The blood vessels were stained with lectin (blue); microglia/macrophages were stained with Ionised Calcium Binding Adapter 1 molecule (Iba-1) (green).

Example 3

Use of Dendrimer-Fluorescent Probes for Longitudinal Imaging of Retinal Inflammation and Oxidative Stress Dendrimer fluorescent probes were investigated for their application in longitudinal imaging of retinal inflammation and oxidative stress. This example demonstrates that dendrimer-FITC (D-FITC) produces better resolution with additional information regarding leaky blood vessels compared to free FITC (fluorescein) in lipid injected rat CNV model. Lipid was injected in brown Norway rats via subretinal injection at day 0 and the fluorescence angiogram imaging was performed on day 21. The rats were anesthetized and administered with sodium fluorescein or D-FITC (5 mg/kg) and the rats were imaged under Micron-3 fundus microscope using a 488 filter at different time points (10 mins, 1 hr and 4 hrs). D-FITC fundus angiography showed that dendrimer biodistribute differently compared to free FITC. Free FITC perfuses and clears from the retina quickly within 1 hr. At early time points (10 mins) post injection free FITC leaked from the retinal blood vessels (FIG. 2, white arrows) in the areas of inflammation causing fluorescence background thereby making in unclear the exact location of the leaky blood vessels. On the other hand, D-FITC angiogram demonstrated spatial resolution showing perfusion only from the leaky blood vessels. Interestingly, this effect was persistent for 4 hrs and beyond whereas free FITC injections resulted in non-specific perfusion and clearance.

A next generation angiography, such as the disclosed dendrimers, using ICG or fluorescein could improve angiography in many ways, such as: (1) clear ICG/FA intact from circulation without metabolism; (2) make them selective to injured areas, so that the affected areas can be clearly delineated; (3) provide a significant contrast; and (4) improve sensitivity enabling quantification of the differences in the extent of DR or AMD between different patients. The dendrimers disclosed herein are tree-like, biocompatible nanostructured polymers that can specifically localize in injured areas of the choroid and the retina, from systemic circulation, while being readily cleared from off target organs through the kidney. The differential ocular distribution of free FITC/ICG and D-FITC/D-ICG in the presence of pathology can significantly enhance angiography for all phases of DR and AMD. Conjugating FITC/ICG to the dendrimer can improve the resolution and quantification of FA and ICGA-based imaging methods.

Dendrimer based fluorescent probes were also investigated for longitudinal imaging of retinal inflammation and oxidative stress because (i) since dendrimer based angiography provides clear insights and exact locations of retinal neovascularization and areas of pathology, and (ii) systemically administered dendrimers target and localize in activated microglia in the areas of inflammation. Accordingly, without wishing to be bound to any one particular theory, it was thought that the disclosed dendrimer probes can be utilized for longitudinal imaging of retinal inflammation and oxidative stress.

For the disclosed dendrimers, multivalency (e.g., multiple —OH groups on the dendrimer surface) can be utilized to conjugate fluorescent agents that can fluoresce in the oxidative stress environment. Since oxidative stress is pronounced in inflammatory cells, by imaging these areas at later time-points clinicians may be provided more profound information regarding the stage of investigated disease, exact coordinates where potential neovascularization can develop. This information may help clinicians for directing lasers in photocoagulation or photodynamic therapy applications. For example, clinicians may be able to identify the neovascular and inflammation areas with improved contrast within the retina which can enable quantification of different grades of neovascularization.

Many probes have been identified such as 4-nitrotyrosine, malonaldehyde, 8-Isoprostane, 7-ethyl-10-hydroxycamptothecin, 4-hydroxy-2-nonenal, etc. that fluoresce in the presence of $H_2O_2$ in cells that are undergoing oxidative stress. These dyes can be conjugated to the dendrimer surface covalently as an additional probe for imaging inflammation and oxidative stress via fluorescence angiography. Scheme 2 (shown below) demonstrates various fluorescent probes for imaging oxidative stress and inflammation.

The differential ocular distribution of free FITC/ICG and D-FITC/D-ICG in the presence of pathology can significantly enhance angiography for all phases of DR and AMD. Conjugating FITC/ICG to the dendrimer can improve the resolution and quantification of FA and ICGA-based imaging methods.

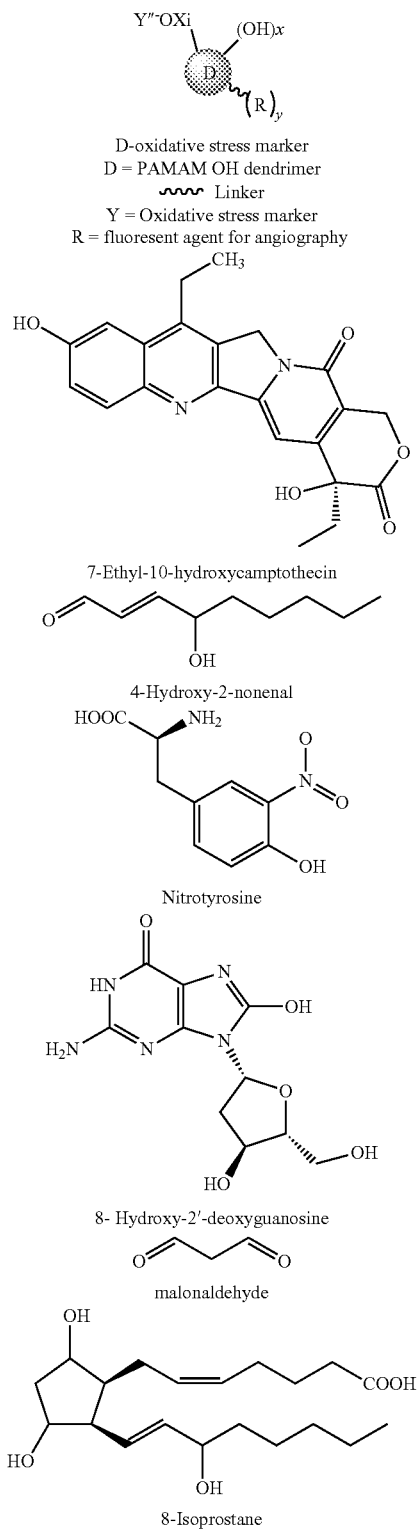

Scheme 2: Dendrimer-Fluorescent Probes Conjugated with Oxidative Stress/Inflammation Markers D-oxidative stress marker
D = PAMAM OH dendrimer
∼∼∼ Linker
Y = Oxidative stress marker
R = fluoresent agent for angiography 7-Ethyl-10-hydroxycamptothecin 4-Hydroxy-2-nonenal Nitrotyrosine 8- Hydroxy-2'-deoxyguanosine malonaldehyde 8-Isoprostane

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Keane P A, Sadda S R. Imaging chorio-retinal vascular disease. Eye. 2010; 24(3):422-7.

Owens S L. Indocyanine green angiography. The British journal of ophthalmology. 1996; 80(3):263.

Klaassen I, Van Noorden C J, Schlingemann R O. Molecular basis of the inner blood-retinal barrier and its breakdown in diabetic macular edema and other pathological conditions. Progress in retinal and eye research. 2013; 31; 34:19-48.

Zhang X, Wang N, Schachat A P, Bao S, Gillies M C. Glucocorticoids: structure, signaling and molecular mechanisms in the treatment of diabetic retinopathy and diabetic macular edema. Curr Mol Med. 2014; 14(3):376-84.

Tang J, Kern T S. Inflammation in diabetic retinopathy. Prog Retin Eye Res. 2011; 30(5):343-58.

Menjoge A R, Kannan R M, Tomalia D A. Dendrimer-based drug and imaging conjugates: design considerations for nanomedical applications. Drug Discov Today. 2010; 15(5-6):171-185.

Mishra M K, Beaty C A, Lesniak W G, Kambhampati S P, Zhang F, Wilson M A, Blue M E, Troncoso J C, Kannan S, Johnston M V, Baumgartner W A, Kannan R M. Dendrimer brain uptake and targeted therapy for brain injury in a large animal model of hypothermic circulatory arrest. ACS Nano. 2014; 8(3):2134-47.

Kannan S, Dai H, Navath R S, Balakrishnan B, Jyoti A, Janisse J, Romero R, Kannan R M. Dendrimer-based postnatal therapy for neuroinflammation and cerebral palsy in a rabbit model. Sci Transl Med. 2012; 4(130):130ra46.

Iezzi R, Guru B R, Glybina I V, Mishra M K, Kennedy A, Kannan R M. Dendrimer-based targeted intravitreal therapy for sustained attenuation of neuroinflammation in retinal degeneration. Biomaterials. 2012; 33(3):979-88.

Sim D A, Chu C J, Selvam S, Powner M B, Liyanage S, Copland D A, Keane P A, Tufail A, Egan C A, Bainbridge J W, Lee R W. A simple method for in vivo labelling of infiltrating leukocytes in the mouse retina using indocyanine green dye. Disease Models and Mechanisms. 2015; 8(11): 1479-87.

Zheng C, Zheng M, Gong P, Jia D, Zhang P, Shi B, Sheng Z, Ma Y, Cai L. Indocyanine green-loaded biodegradable tumor targeting nanoprobes for in vitro and in vivo imaging. Biomaterials. 2012; 33(22):5603-9.

Desmettre T, Devoisselle J M, Mordon S. Fluorescence properties and metabolic features of indocyanine green (ICG) as related to angiography. Survey of ophthalmology. 2000; 45(1):15-27.

Sevick-Muraca E M, Houston J P, Gurfinkel M. Fluorescence-enhanced, near infrared diagnostic imaging with contrast agents. Current opinion in chemical biology. 2002; 6(5):642-50.

Baba T, Bhutto I A, Merges C, Grebe R, Emmert D, McLeod D S, Armstrong D, Lutty G A. A rat model for choroidal neovascularization using subretinal lipid hydroperoxide injection. Am J Pathol. 2010; 176(6):3085-3097.

Kambhampati S P, Clunies-Ross A J, Bhutto I, Mishra M K, Edwards M, McLeod D S, Kannan R M, Lutty G. Systemic and Intravitreal Delivery of Dendrimers to Activated Microglia/Macrophage in Ischemia/Reperfusion Mouse Retinal Microglia Uptake of Dendrimers. Investigative ophthalmology & visual science. 2015 Jul. 1; 56(8): 4413-24.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A dendrimer of formula (I):

$$\underset{(Y)_p}{\overset{(OH)_m}{X}} {\left( O \overset{O}{\underset{\|}{C}} L^1 - S - L^2 - \underset{|}{\overset{R^1}{N}} - Z \right)}_n, \quad (I)$$

wherein,
X is a G2 to G10 poly(amidoamine) (PAMAM) dendrimer;
$L^1$ and $L^2$ are each independently $C_1$-$C_{12}$ alkylenyl, $C_2$-$C_{12}$ alkenylenyl, or $C_2$-$C_{12}$ alkynylenyl;
Z is a fluorophore;
Y is an oxidative stress probe;
$R^1$ is hydrogen or alkyl;
n is an integer from 1 to 100;
p is an integer from 0 to 100; and
m is an integer from 1 to 4000.

2. The dendrimer of claim 1, wherein
X is a G2 to G6 PAMAM dendrimer;
$L^1$ and $L^2$ are each independently $C_1$-$C_6$ alkylenyl, $C_2$-$C_6$ alkenylenyl, or $C_2$-$C_6$ alkynylenyl;
n is an integer from 1 to 10;
p is an integer from 1 to 10; and
m is an integer from 1 to 250.

3. The dendrimer of claim 1, wherein
$L^1$ and $L^2$ are each independently $C_1$-$C_6$ alkylenyl;
n is an integer from 1 to 5; and
p is an integer from 1 to 5.

4. The dendrimer of claim 1, wherein Y, at each occurrence, is independently selected from the group consisting of 7-ethyl-10-hydroxycamptothecin, 4-hydroxy-2-nonenal, nitrotyrosine, 8-hydroxy-2'-deoxyguanosine, malonaldehyde, and 8-isoprostane.

5. The dendrimer of claim 1 having formula (I-a):

$$\overset{(OH)_m}{X} {\left( O \overset{O}{\underset{\|}{C}} L^1 - S - L^2 - \overset{H}{\underset{|}{N}} - Z \right)}_n, \quad (I\text{-}a)$$

wherein,
X is a G2 to G10 poly(amidoamine) (PAMAM) dendrimer;
$L^1$ and $L^2$ are each independently $C_1$-$C_{12}$ alkylenyl, $C_2$-$C_{12}$ alkenylenyl, or $C_2$-$C_{12}$ alkynylenyl;
Z is a fluorophore;
n is an integer from 1 to 100; and
m is an integer from 1 to 4000.

6. The dendrimer of claim 5, wherein:
X is a G2 to G6 PAMAM dendrimer;
$L^1$ and $L^2$ are each independently $C_1$-$C_6$ alkylenyl, $C_2$-$C_6$ alkenylenyl, or $C_2$-$C_6$ alkynylenyl;
n is an integer from 1 to 10; and
m is an integer from 1 to 250.

7. The dendrimer of claim 1, wherein:
$L^1$ and $L^2$ are each independently $C_1$-$C_6$ alkylenyl; and
n is an integer from 1 to 5.

8. The dendrimer of claim 1 having formula (I-b):

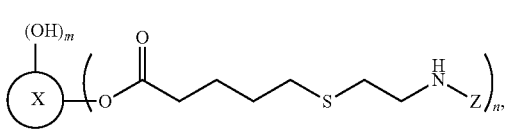

(I-b)

wherein,
X is a G2 to G10 PAMAM dendrimer;
Z is a fluorophore;
n is an integer from 1 to 100; and
m is an integer from 1 to 4000.

9. The dendrimer of claim 8, wherein
X is a G2 to G6 PAMAM dendrimer;
n is an integer from 1 to 10; and
m is an integer from 1 to 250.

10. The dendrimer of claim 1, wherein
X is a G4 PAMAM dendrimer;
n is 2; and
m is 62.

11. The dendrimer of claim 1, wherein Z, at each occurrence, is independently selected from the group consisting of indocyanine green, fluorescein isothiocyanate, boron-dipyrromethene, rhodamine, and rose Bengal.

12. The dendrimer of claim 1, wherein the dendrimer is:

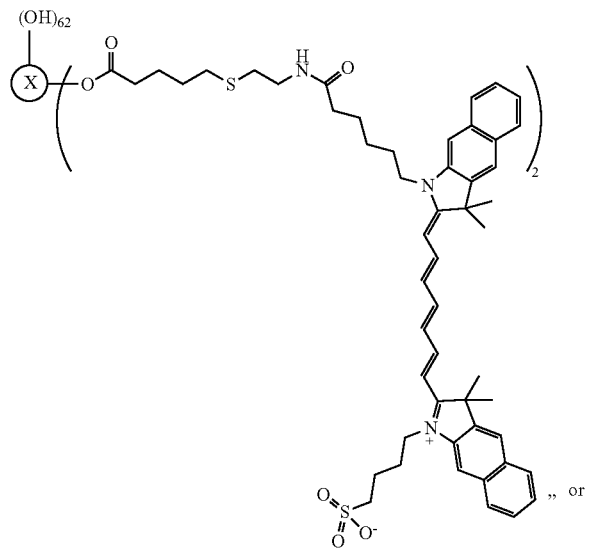

, or

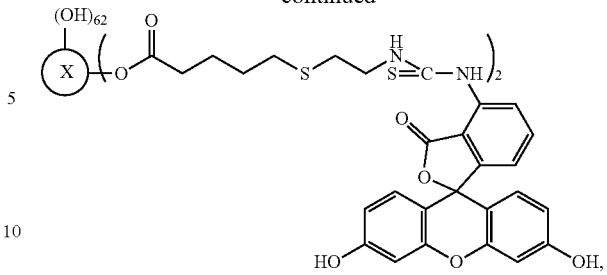

wherein X is a G4 PAMAM dendrimer.

13. The dendrimer of claim 1, wherein the dendrimer has a diameter of from about 1 nm to about 20 nm.

14. The dendrimer of claim 1, wherein between about 0.1% and about 20% of the terminal groups of the dendrimer are covalently linked to a fluorophore.

15. A method for performing angiography on a subject in need thereof, the method comprising:
administering a composition to the subject, the composition comprising the dendrimer of claim 1; and
observing and/or quantifying the fluorescence emitted in the subject's eye vasculature.

16. The method of claim 15, wherein the subject has macular degeneration (AMD), retinitis pigmentosa, optic neuritis, infection, uveitis, sarcoid, sickle cell disease, retinal detachment, temporal arteritis, retinal ischemia, choroidal ischemia, choroidal ischemia, ischemic optic neuropathy, arteriosclerotic retinopathy, hypertensive retinopathy, retinal artery blockage, retinal vein blockage, hypotension, diabetic retinopathy, macular edema, choroidal neovascularization, or a combination thereof.

17. The method of claim 15, wherein the composition comprises a first set of dendrimers having a size of between about 2 nm and about 8 nm and a second set of dendrimers having a size about 12 nm and about 20 nm.

18. The method of claim 15, wherein administering the composition includes injecting the composition intravenously into the vasculature of the subject.

19. The method of claim 15, wherein the composition is administered at a dosage of between about 0.1 mg/kg and about 20 mg/kg.

20. The method of claim 15, wherein the method is performed over a period of between about 10 seconds and about 28 days.

21. The method of claim 15, wherein the method comprises a single administration of the composition and is performed for at least 21 days.

22. The method of claim 15, wherein the method further comprises performing optical coherence tomography (OCT) on the subject.

23. The method of claim 15, wherein the method further comprises identifying diseased vasculature.

24. The method of claim 23, wherein the method further comprises identifying the disease stage of the diseased vasculature.

25. The method of claim 15, wherein the composition further comprises a pharmaceutical acceptable carrier.

26. The method of claim 15, wherein the method further comprises identifying the subject as in need of treatment for an eye disease.

27. The method of claim 26, wherein the method further comprises administering an effective amount of a therapeutic agent to the subject identified as in need of treatment for an eye disease.

28. The method of claim 27, wherein the therapeutic agent comprises triamcinolone acetonide, methyl prednisone, dexamethasone, COX-2 inhibitors, gold compound anti-inflammatory agents, salicylate anti-inflammatory agents, N-acetyl cysteine, minocycline, aflibercept, rapamycin, anti-VEGF agents, or a combination thereof.

29. A pharmaceutical composition comprising the dendrimer of claim 1; and a pharmaceutical acceptable carrier.

30. An angiography kit comprising:
the pharmaceutical composition of claim 29; and
instructions for using the pharmaceutical composition in angiography.

* * * * *